United States Patent [19]

Shimizu et al.

[11] Patent Number: 4,937,375
[45] Date of Patent: Jun. 26, 1990

[54] (PHENYLETHENYL)PHENYLPROPIONIC ACID AND ITS ESTER, AND METHOD FOR PRODUCING (BENZOYLPHENYL)PROPIONIC ACID OR ITS ESTER

[75] Inventors: Isoo Shimizu; Yasuo Matsumura, both of Yokohama; Yutaka Arai, Tokyo, all of Japan

[73] Assignee: Nippon Petrochemicals Company, Limited, Tokyo, Japan

[21] Appl. No.: 165,729

[22] Filed: Mar. 9, 1988

[30] Foreign Application Priority Data

Mar. 12, 1987 [JP] Japan .................................. 62-57099

[51] Int. Cl.$^5$ ............................................ C07C 143/02
[52] U.S. Cl. ...................................... 560/101; 562/491
[58] Field of Search ......................... 560/101; 562/491

[56] References Cited

PUBLICATIONS

Dive et al., *Chemical Abstracts*, vol. 86, No. 188939r (1977).

*Primary Examiner*—Bruce Gray
*Attorney, Agent, or Firm*—Scully, Scott, Murphy & Presser

[57] ABSTRACT

New compounds of α-(3-(1-phenylethenyl)phenyl)-propionic acid and its esters and a method for producing α-(3-benzoylphenyl)propionic acid which is prepared by oxidizing the former compound as an intermediate. The method is characterized in the easiness in operation, the low cost and the high purity of the product.

2 Claims, No Drawings

(PHENYLETHENYL)PHENYLPROPIONIC ACID AND ITS ESTER, AND METHOD FOR PRODUCING (BENZOYLPHENYL)PROPIONIC ACID OR ITS ESTER

BACKGROUND OF THE INVENTION

1. Field of the Invention

This invention relates to α-(3-(1-phenylethenyl)phenyl)propionic acid or or its ester which is represented by the following formula (II) and further relates to a method for producing α-(3-benzoylphenyl)propionic acid or its ester which is represented by the following formula (I) using the former new compound as an intermediate.

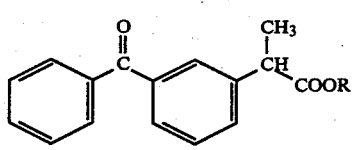
(I)

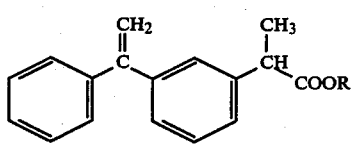
(II)

α-(3-(1-phenylethenyl)phenyl)propionic acid and its ester (formula II) are intermediates used for economically preparing α-(3-benzoylphenyl)propionic acid (tradename: ketoprofen) which is represented by the following formula (I-a) and is used as a medicine for the relief of pain, fever and inflammation.

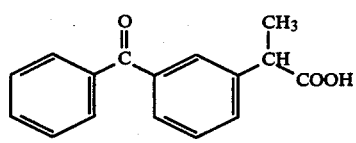
(I-a)

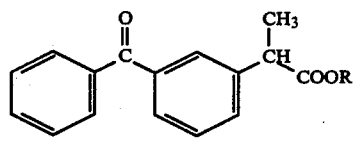
(I-b)

wherein R is an alkyl group having 1 to 4 carbon atoms.

The above ester of the formula (I-b) is easily hydrolyzed to produce α-(3-benzoylphenyl)propionic acid.

2. Description of the Prior Art

With regard to the preparation of ketoprofen, various methods have been proposed. Typical methods of them are exemplified as follows:

(1) Ketoprofen is prepared in a high yield by reacting 3-vinylbenzophenone with carbon monoxide in dilute hydrochloric acid in the presence of a palladium catalyst (U.S. Pat. No. 4,329,507).

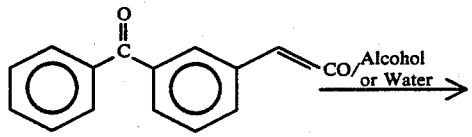

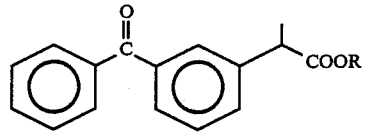

(2) 4-Acetylbenzophenone is reacted with chloroform in a basic condition in the presence of tertiary ammonium salt to obtain α-arylpropenoic acid and it is then subjected to catalytic hydrogenation reduction in the presence of palladium-carbon catalyst to obtain ketoprofen (Japanese Laid-Open Patent Publication No. 55-7225).

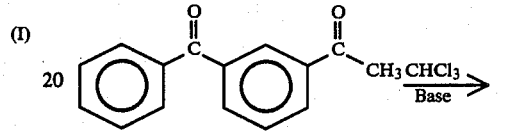

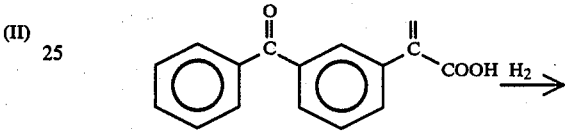

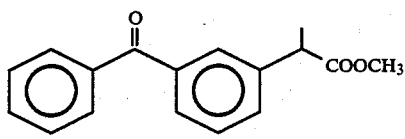

(3) 3-Benzoylpropiophenone is reacted with orthomethyl formate in the presence of thallium nitrate to produce the methyl ester of ketoprofen (British Patent No. 2,019,393).

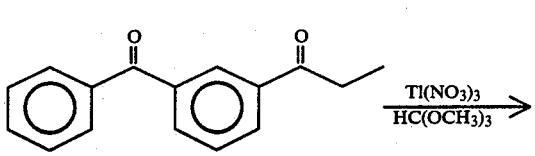

(4) 3-Benzylacetophenone is reacted with ethyl chloroactate in the presence of a strong base to produce glycidic acid ester. This compound is then treated with an aqueous solution of sodium hydroxide to obtain a hydrolyzed and decarboxylated product of α-(3-benzylphenyl)propionaldehyde and it is further oxidized with potassium permanganate to obtain the ketoprofen (Japanese Laid-Open Patent Publication No. 55-36450).

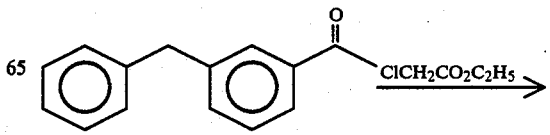

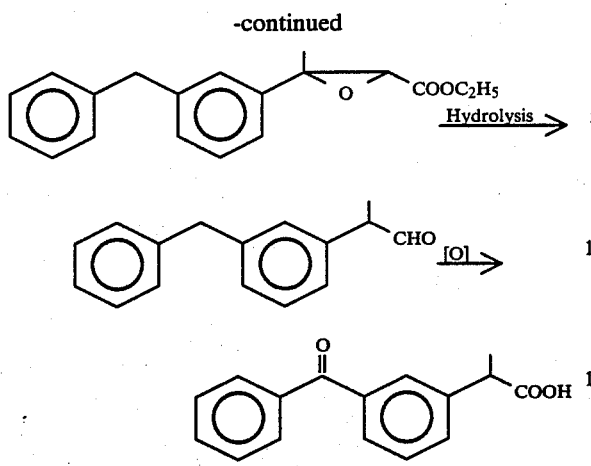

In both the above methods (1) and (2), the numbers of reaction steps are small and the aimed product can be obtaine in high yields. It cannot be said, however, that the synthesis of starting materials is easy.

With regard to the method (3), even though the reaction process is short, it cannot be said that the preparation of the raw material is easy and safe because the toxic thallium compound is used. Furthermore, it cannot be said that the starting material used in the method (4) is easily available. Accordingly, these methods (1) to (4) are not satisfactory in view of industrial production.

BRIEF SUMMARY OF THE INVENTION

It is, therefore, the primary object of the present invention to provide a new intermediate which is useful for synthesizing ketoprofen without difficulty in a high yield and at a low cost using easily available raw materials.

Another aspect of the present invention is to provide a novel method for producing the α-(3-benzoylphenyl)-propionic acid or its alkyl ester using this new intermediate compound.

That is, the present invention relates to α-(3-(1-phenylethenyl)phenyl)propionic acid and its ester represented by the formula (II) and a novel method for producing α-(3-benzoylphenyl)propionic acid or its alkyl ester represented by the formula (I) which is characterized in that the new compound of the formula (II) is oxidized.

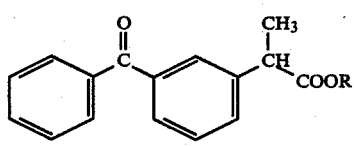

wherein R is a hydrogen atom or an alkyl group having 1 to 4 carbon atoms.

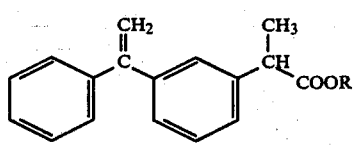

wherein R is a hydrogen atom or an alkyl group having 1 to 4 carbon atoms.

DETAILED DESCRIPTION OF THE INVENTION

Exemplified as the compounds represented by the foregoing formula (II) are α-(3-(1-phenylethenyl)phenyl)propionic acid, α-(3-(1-phenylethenyl)phenyl)propionic acid methyl ester, α-(3-(1-phenylethenyl)phenyl)propionic acid ethyl ester, α-(3-(1-phenylethenyl)phenyl)propionic acid propyl ester, α-(3-(1-phenylethenyl)phenyl)propionic acid isopropyl ester, α-(3-(1-phenylethenyl)phenyl)propionic acid n-butyl ester, α-(3-(1-phenylethenyl)phenyl)propionic acid sec-butyl ester, α-(3-(1-phenylethenyl)phenyl)propionic acid tert-butyl ester, and α-(3-(1-phenylethenyl)phenyl)propionic acid isobutyl ester. In these compounds, the optically active isomers of them are also included.

The foregoing α-(3-(1-phenylethenyl)phenyl)propionic acid and its esters can be prepared from 1-(3-vinylphenyl)-1-phenylethylene of the following formula (III) by the known method of hydroesterification.

The 1-(3-vinylphenyl)-1-phenylethylene of the formula (III) is prepared without difficulty by, for example, the following procedure.

A method to use acetophenone as a starting material will be described. Acetophenone is reacted with a Grignard reagent of m-vinylphenylmagnesium bromide to obtain 1-(3-vinylphenyl)-1-phenylethyl alcohol (formula IV) (hereinafter referred to as "VPA"). The reaction product is then dehydrated in the presence of potassium hydrogensulfate to form 1-(3-vinylphenyl)-1-phenylethylene (formula III). This Grignard addition reaction is carried out at a temperature in the range of 0° to 100° C., preferably 20° to 80° C. The dehydration is carried out at 170° to 250° C., preferably 190° to 230° C., at a reduced pressure. The quantity of Grignard reagent is 1.0 to 1.2 equivalents relative to the acetophenone.

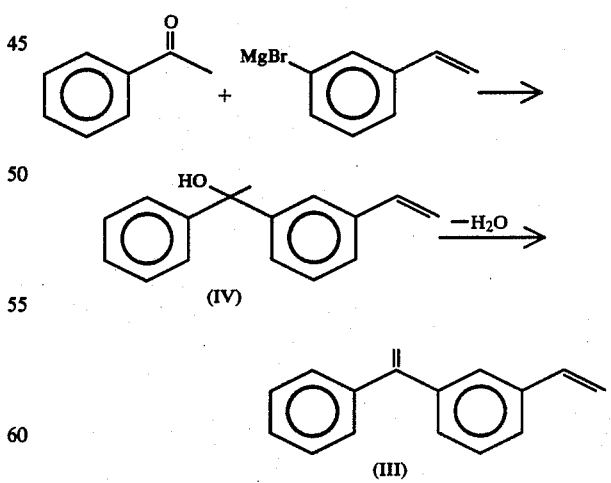

The carbonyl compound of the formula (II), α-(3-(1-phenylethenyl)phenyl)propionic acid and its ester can be obtained by subjecting the thus obtained -(3-vinylphenyl)-1-phenylethylene to the well known reaction of hydroesterification.

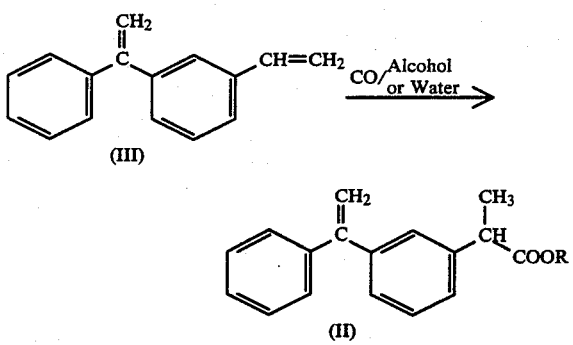

(III)

(II)

The novel metal complex catalysts which are used for the above hydroesterification are the complexes of Pd, Rh and Ir, and the complex of Pd is especially preferable. These noble metal complexes have ligands of halogen atoms, trivalent phosphorus compounds, or carbonyl compound such as carbon monoxide. Usable noble metal, for example, palladium includes those of zero-valent to divalent.

The typical catalysts are exemplified by bistriphenylphosphine dichloropalladium, bistributylphosphine dichloropalladium, bistricyclohexylphosphine dichloropalladium π-allyltriphenylphosphine dichloropalladium, triphenylphosphine, piperidine dichloropalladium, bisbenzonitrile dichloropalladium, biscyclohexyloxime dichloropalladium, 1,5,9-cyclododecatriene dichloropalladium, bistriphenylphosphine dicarbonyl palladium, bistriphenylphosphine acetate palladium, bistriphenylphosphine dinitrate palladium, bistriphenylphosphine palladium sulfate, and tetrakistriphenylphosphine palladium.

In the use of the catalyst, it is added to the reaction system in the form of a complex. While, it is also possible to add a ligand separately so as to form a complex in the reaction system.

The use quantity the catalyst is 0.0001 to 0.5 mole, preferably 0.001 to 0.1 mole to one mole of 1-(3-vinylphenyl)-1-phenylethylene (formula III). The addition quantity of the compound to form the ligand is 0.8 to 10 moles, preferably 1 to 4 moles, to 1.0 mole of the noble metal of Pd, Rh or Ir to form the nuclei of complex.

The hydroesterification is carried out at a temperature in the range of 40° to 150° C., preferably 70° to 120° C. The pressure of carbon monoxide is 20 to 700 kg/cm², and preferably 40 to 500 kg/cm². In order to accelerate the reaction, an acid such as hydrogen chloride or boron trifluoride can be added.

In the hydroesterification, when 1-(3-vinylphenyl)-1-phenylethylene of the formula (III) is reacted in the presence of water with carbon monoxide, a carboxylic acid, ketoprofen, in which the R in the formula (II) is a hydrogen atom is obtained. When the reaction is carried out in the presence of a lower alcohol having an alkyl group, an alkyl ester in which the R in the formula (II) is the alkyl group of the lower alcohol can be obtained. For example, in the case of methyl alcohol, methyl ester is formed.

The alcohols are lower alcohols having 1 to 4 carbon atoms such as methyl alcohol, ethyl alcohol, n-propyl alcohol, isopropyl alcohol, n-butyl alcohol, sec-butyl alcohol, tert-butyl alcohol, and isobutyl alcohol.

The foregoing hydroesterification products are exemplified by α-(3-(1-phenylethenyl)phenyl)propionic acid, α-(3-(1-phenylethenyl)phenyl)propionic acid methyl ester, α-(3-(1-phenylethenyl)phenyl)propionic acid ethyl ester, α-(3-(1-phenylethenyl)phenyl)propionic acid propyl ester, α-(3-(1-phenylethenyl)phenyl)propionic acid isopropyl ester, α-(3-(1-phenylethenyl)phenyl)propionic acid n-butyl ester, α-(3-(1-phenylethenyl)phenyl)propionic acid sec-butyl ester, α-(3-(1-phenylethenyl)phenyl)propionic acid tert-butyl ester and α-(3-(1-phenylethenyl)phenyl)propionic acid isobutyl ester. In these compounds, the optically active isomers of them are also included.

After the hydroesterification, the catalyst and the aimed product of α-(3-(1-phenylethenyl)phenyl)propionic acid or its ester of the formula (II) can be easily separated by distilling, preferably under reduced pressure, the reaction product. The recovered complex catalyst can be used again.

The α-(3-(1-phenylethenyl)phenyl)propionic acid or its ester of the formula (II) is a new compound. This compound can be prepared by the following method more easily and more economically.

When benzene is alkylated with ethylene in the presence of an alkylation catalyst to obtain ethylbenzene as well as the fraction containing 1-(3-ethylphenyl)-1-phenylethane (formula V). The fraction containing 1-(3-ethylphenyl)-1-phenylethane is then dehydrogenated in the presence of a dehydrogenation catalyst to obtain a fraction containing 1-(3-vinylphenyl)-1-phenylethylene (formula III). By the hydroesterification of this fraction in a conventional manner, α-(3-(1-phenylethenyl)phenyl)propionic acid or its alkyl ester of the formula (II) can be prepared.

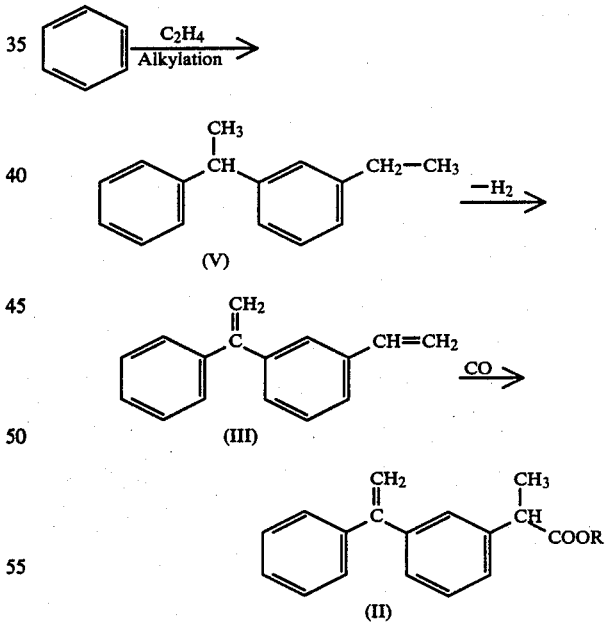

The above will be described in more detail.

When benzene is alkylated with ethylene in the presence of an alkylation catalyst, a reaction product containing unreacted benzene, alkylbenzenes, polyalkylbenzenes and heavier products is obtained. The above 1-(3-ethylphenyl)-1-phenylethane of the formula (V) is recovered as a fraction mainly containing components having a boiling point of 285° to 290° C. (atmospheric pressure basis) by distillation such as reduced-pressure distillation. The fraction is then dehydrogenated in the presence of a dehydrogenation catalyst, and if necessary, it is followed by distillation, to obtain 1-(3-vinylphenyl)-1-phenylethylene of the formula (III).

Exemplified as the catalysts for the above alkylation of benzene are Lewis acids such as metal halide like aluminum chloride, iron chloride and boron trifluoride; protonic acids such as hydrogen fluoride and phosphoric acid; and solid acids such as silica-alumina and crystalline alumino-silicate of ZSM-5 type synthetic zeolite. In addition, solid catalysts such as the one in which a protonic acid like phosphoric acid is carried on a carrier like diatomaceous earth, can be exemplified. Especially preferable catalysts are metal halides such as aluminum chloride and ZSM-5 type synthetic zeolite catalysts, known as ZSM-5 and ZSM-11.

These ZSM-5 type synthetic zeolites are described in detail in the following patent gazettes.

ZSM-5: U.S. Pat. No. 3,702,886; and British Pat. No. 1,161,974

ZSM-11: U.S. Pat. No. 3,709,979

In general, the molar ratio as $SiO_2/Al_2O_3$ of the ZSM-5 type catalysts are 20 to 400 and the catalysts exhibit specific X-ray diffraction patterns. Detailed description is given in the above patent gazettes.

The synthetic zeolites used in the present invention are those which are ion-exchanged with hydrogen ion or divalent ions such as calcium, magnesium, strontium and barium ions, or trivalent ions such as the ions of rare earth elements of cerium and yttrium. Besides them, the synthetic zeolites which are chemically modified with boron, gallium, phosphorus or their compounds can also be used.

The alkylation of benzene with ethylene can be carried out in a vapor phase and a liquid phase. For example, the temperature as a condition for alkylation in vapor phase is in the range of 300° to 650° C., preferably 350° to 550° C. The pressure for the alkylation is not especially limited. However, the reaction is generally performed at 1 to 100 kg/cm$^2$ and preferably at atmospheric pressure. The preferable molar ratio of materials as "ethylene/benzene" to be fed to the reaction system is 0.05 to 5. The value of WHSV is in the range of 1 to 500 and preferably 1 to 300.

In the reaction in liquid phase, the reaction temperature is about 20° to 175° C. and preferably about 90° to 150° C. The reaction pressure may be a value at which the reaction system can be maintained in a liquid phase, for example, about 0.5 to 14 kg/cm$^2$. The duration of reaction is generally in the range of about 10 minutes to 10 hours, and preferably about 20 minutes to 3 hours.

By alkylating benzene with ethylene, a reaction mixture which comprises unreacted benzene, ethylbenzenes, polyethylbenzenes and heavier products, is obtained. In this heavier products, the 1-(3-ethylphenyl)-phenylethane and also tarry substance are contained.

From the heavier products which are recovered from the above reaction products, or from the reaction product directly, a fraction containing 1-(3-ethylphenyl)-1-phenylethane is recovered by distillation such as reduced pressure distillation. The fraction containing 1-(3-ethylphenyl)-1-phenylethane is obtained as a fraction having a boiling point of 285° to 290° C. (as atmospheric pressure).

As the above-described alkylation reaction can be exemplified by the process of preparing ethylbenzene which is widely adopted for the industrial preparation of styrene by dehydrogenation of the ethylbenzene. For example, in industrial methods, an aluminum chloride process using aluminum chloride catalyst, a high-pressure process using alumina catalyst carried on silica gel that was developed by Koppers Gmbh, a solid phosphoric acid process using a solid catalyst in which phosphoric acid is impregnated in diatomaceous earth that was developed by Universal Oil Products Co., an alkar process using a catalyst of boron fluoride or its complex also developed by the above U.O.P. CO., and a zeolite process using a zeolite catalyst that was developed by Mobil Oil Corp.

DEHYDROGENATION REACTION

In the present invention, the fraction containing the above 1-(3-ethylphenyl)-1-phenylethane is subjected to dehydrogenation in the presence of a dehydrogenation catalyst. As the dehydrogenation catalyst for this purpose, the conventional catalysts that are used in the dehydrogenation of ethylbenzene to prepare styrene can be used. For example, a catalyst containing iron, chromium or mixture thereof such as chromia-alumina catalyst and iron oxide catalyst can be used. These catalysts can be used together with a promoter such as potassium carbonate or the oxide of chromium, cerium, molybdenum or vanadium.

As the dehydrogenation is an equilibrium reaction, when the pressure as a reaction condition is low, the reaction can proceed further. With regard to temperature, the higher the temperature is, the further the reaction proceeds because it is an endothermic reaction. Accordingly, the reaction temperature is generally selected from the range of 500° to 700° C., and preferably 550° to 650° C. At a temperature below 500° C., the dehydrogenation reaction cannot substantially proceed. On the other hand, temperatures above 700° C. is not desirable because side reactions such as decomposition is caused to occur. The reaction pressure is from a reduced pressure to 5 kg/cm$^2$, and preferably from a reduced pressure to 3 kg/cm$^2$. In general, excess steam is used as a heating medium.

The reaction time length in a continuous flow system is selected from the range of 0.01 to 10 hr$^{-1}$ as LHSV.

After the reaction, 1-(3-vinylphenyl)-1-phenylethylene is obtained by distillation, preferably by reduced pressure distillation.

Because the 1-(3-vinylphenyl)-1-phenylethylene obtained by the dehydrogenation has a higher boiling point as compared with that of the saturated compounds in the starting materials, the separation by distillation can be performed more easily.

The thus obtained 1-(3-vinylphenyl)-1-phenylethylene is then subjected to hydroesterification in the presence of carbon monoxide and water or an alcohol in a conventional manner to prepare α-(3-(1-phenylethenyl)phenyl)propionic acid or its alkyl ester.

The thus obtained α-(3-(1-phenylethenyl)phenyl)propionic acid or its ester (formula II) is then oxidized to prepare α-(3-benozylphenyl)propionic acid, i.e. ketoprofen, or its ester without difficulty. In the case that the oxidation product is an ester, it is easily hydrolyzed to obtain the α-(3-benzoylphenyl)propionic acid. When the ester is oxidized, it is also possible that the ester is previously converted into the form of an acid by hydrolysis.

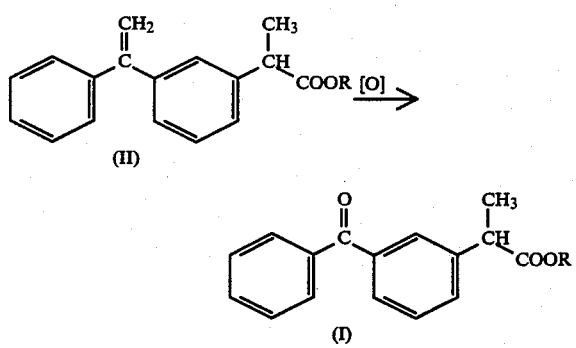

wherein R is a hydrogen atom or an alkyl group having 1 to 4 carbon atoms.

OXIDATION

The oxidation will be described in detail.

In the oxidation of α-(3-(1-phenylethenyl)phenyl)-propionic acid or its ester (formula II), the ethylidene group of the compound is easily oxidized without affecting its acid or ester side. In this process, it is important that the carboxyl group and the ester group should not be influenced.

The above oxidation can be done according to a conventional oxidation method. For example, there are an oxidation method with molecular oxygen in the presence of an oxidation catalyst and another oxidation method using an oxidizing agent such as permanganate, manganese dioxide, chromate, lead tetraacetate, periodate, ruthenium tetraoxide, osmium tetraoxide, hydrogen peroxide, selenium dioxide, ozone, and a mixture of them. By carrying out the oxidation by one or a combination of two or more of these methods, α-(3-benzoylphenyl)propionic acid or its alkyl ester (ketrofen, formula I) can be obtained from the α-(3-(1-phenylethenyl)phenyl)propionic acid or its ester (formula II). Both the oxidation of α-(3-(1-phenylethenyl)phenyl)-propionic acid and the oxidation of the ester of α-(3-(1-phenylethenyl)phenyl)propionic acid are possible.

The catalyst used in the oxidation with molecular oxygen are exemplified by the salts of metals selected from the groups of VI-B, VII-B and VIII of the periodic table such as chromium, manganese, tungsten, molybdenum, platinum, palladium, cobalt, nickel, iron, rhodium, and ruthenium, or their mixtures. Among them, the salts of cobalt, iron, manganese, and chromium are preferable. The suitable quantity of a catalyst to be used is 0.05 to 10% by weight to the quantity of raw material. As the molecular oxygen, pure oxygen or the air can be used. Furthermore, it is possible to supply the reaction system with a mixture of pure oxygen and other inert gases.

The reaction temperature in the oxidation using molecular oxygen is 30° to 250° C., and preferably 50° to 200° C. In the case that the reaction temperature is lower than 30° C., the rate of reaction is very low, and in the case that the reaction temperature exceeds 250° C., the selectivity to the aimed product is seriously lowered, both of which are not desirable.

In order to improve the efficiency in the contact of starting materials with an oxidizing agent, a solvent can be used. Such a solvent is exemplified by water, acetone, alcohols such as tert-butyl alcohol, glacial acetic acid, acetic acid, isooctane, benzene, chloroform, and pyridine. They are used singly or as a mixture of them.

The quantity of oxidizing agent such as a permanganate to be added is at least 1 equivalent, preferably more than 1.5 equivalent, to the raw material. There is not especially the upper limit of the use quantity, however, the quantity of more than 10 equivalent is not desirable because it is uneconomical. The temperature of oxidation using the oxidizing agent is 0° to 200° C. and preferably 30° to 150° C. The reaction cannot proceed at temperatures below 0° C., while by-products are formed and the selectivity to the aimed product is seriously lowered at temperatures above 200° C., both of which are not desirable.

It is, in either case, a remarkable feature of the compound of formula (II) that its only ethylidene group is easily oxidized with no change of its carbonyl part.

After the oxidation, the oxidizing agent or oxidation catalyst is separated, for example, by filtration, or the reaction mixture is extracted with an organic solvent such as benzene, ethyl acetate, or chloroform. After that, highly pure α-(3-benzoylphenyl)propionic acid, i.e. ketoprofen, or its alkyl ester is obtained by the conventional distillation or recrystallization. In the case that the oxidation product is an ester, it is hydrolyzed and refined in the conventional method to obtain easily a highly pure α-(3-benzoylphenyl)propionic acid.

As described above in detail, it is possible to prepare easily ketoprofen at low cost and in a high yield by using the new compound of α-(3-(1-phenylethenyl)-phenyl)propionic acid or its ester as an intermediate, which is proposed in the present invention. Because substituent groups of the compound according to the present invention are specified, ketoprofen having particular effect to relief inflammation can be produced at low cost without difficulty by using the compound as an intermediate.

In addition, when the method of the present invention is put into practice starting the alkylation of benzene, an increased advantage of the invention can be expected.

The present invention will be described with reference to examples which by no means limit the present invention.

EXAMPLE 1

Synthesis of 1-(3-vinylphenyl)-1-phenylethylene (formula III)-(1)

To a 2 liter three-neck flask equipped with a dropping funnel, a reflux condenser and a stirrer was added 25.5 g (1.05 mole) of metallic magnesium and it was dried sufficiently to supplying dry nitrogen gas. After that, 50 ml of tetrahydrofuran which has been dried with a molecular sieve 5A, was put into the flask and the contents were stirred vigorously. A solution of 183 g (1.0 mole) of 3-vinylbenzene bromide in 500 ml of dried tetrahydrofuran was dropped little by little over 2 hours. The reaction temperature was maintained 75° to 80° C. and, after the addition of the solution, the stirring was continued for further 1 hour as it stands. Into the thus obtained Grignard reagent of 3-vinylphenylmagnesium bromide, a solution of 122.6 g (1.02 mole) of acetophenone in 500 ml of dried tetrahydrofuran was dropped little by little for 2 hours. The reaction temperature was maintained at 75° to 80° C. and, after the dropping, the stirring was continued for further 1 hour as it stands. The reaction mixture was then poured into 3 liter of an aqueous solution of 75 g of ammonium chloride and it was left to stand still for 20 hours and an oily layer was recovered to obtain 1-(3-vinylphenyl)-1-phenylethyl alcohol (VPA: formula (IV)) in a yield 89% (acetophenone basis) by distilling off the tetrahydrofuran.

To a 300 ml tree-neck flask with a distillation column and a dropping funnel was added 81 g of potassium hydrogensulfate and the pressure was reduced to 15 to 20 mmHg. The obtained alcohol was then dropped into the flask little by little over 2 hours. The water and oily components produced by dehydration were recovered from the top of the distillation column and 1-(3vinylphenyl)-1-phenylethylene was obtained in a yield of 100% (VPA) basis) from the oily layer by a separatory funnel. The dehydration reaction was carried out at a temperature of 200° to 250° C.

The analytical data on the thus produced 1-(3-vinylphenyl)-1-phenylethylene (formula III) are shown in the following:

Boiling Point: 134.0°–135.5° C./2–3 mmHg
IR: (Neat) cm$^{-1}$ 3050, 1690, 1495, 1260, 995, 900; 810, 780, 700.
$^1$H-NMR: (CCl$_4$, δppm) 7.10–7.70 (9H Multiplet); 6.65–6.80 (1H Quadruplet); 5.65–5.80 (1H, Doublet); 5.45–5.50 (2H Doublet); 5.20–5.30 (1H Doublet).
Elemental Analysis: (as C$_{16}$H$_{14}$)
Calculated: C: 93.20%; H 6.80%.
Found: C: 93.24%; H: 6.76%.

EXAMPLE 2

Synthesis of α-(3-(1-phenylethenyl)phenyl)propionic acid

To a 500 ml autoclave with a stirrer were added 43 g of 1-(3-vinylphenyl)-1-phenylethylene, 5.5 g of bistriphenylphosphine dichloropalladium, 80 g of 10% aqueous solution of hydrochloric acid and 80 ml of toluene as a solvent. After the pressure was raised up to 100 kg/cm$^2$ by carbon monoxide at room temperature, with raising the temperature at 120° C., the pressure was raised to 300 kg/cm$^2$. After the absorption of carbon monoxide by the reaction was ceased, the reaction was still continued for 24 hours.

After the reaction, the autoclave was cooled and reaction mixture was recovered and the oily layer and aqueous layer were separated by a separatory funnel. The oily layer was extracted three times with 50 ml of 8% aqueous solution of sodium hydroxide. The aqueous extract solution were combined with the above separated aqueous layer and the pH was adjusted to 2 with hydrochloric acid. After that extraction was done three times with 500 ml of chloroform. The chloroform was removed from the extract liquid by reduced pressure evaporation to obtain 44.7 g of the compound of the above title.

The analytical results of α-(3-(1-phenylethenyl)phenyl)propionic acid are shown in the following.

The analytical results are the same as those of α-(3-(1-phenylethenyl)phenyl)propionic acid which was obtained by hydrolyzing α-(3-(1-phenylethenyl)phenyl)-propionic acid methyl ester by a conventional method in Example 4.

Property: Melting Point 69.0°–71.0° C.
IR: (Neat) cm$^{-1}$ 3030, 2750, 2650, 1715, 1610, 1420; 1240, 1070, 910, 785, 710.
$^1$H-NMR: (CCl$_4$, δppm) 12.2 (1H Singlet); 6.80–7.50 (9H, Multiplet); 5.38 (2H Singlet); 3.45–3.90 (1H Quadruplet); 1.35–1.65 (3H, Doublet).
Elemental Analysis: (as C$_{17}$H$_{16}$O$_2$)
Calculated: C: 80.95%; H: 6.35%; O: 12.70%.
Found: C: 80.91%; H: 6.32%; O: 12.77%.

EXAMPLE 3

Synthesis of 1-(3-vinylphenyl)-1-phenylethylene (formula III)-(2)

Alkylation

From the reaction mixture in ethylbenzene preparation process for producing polystyrene by reacting benzene with ethylene using aluminum chloride catalyst, a fraction having a boiling point of 285°–290° C. as atmospheric pressure) was recovered by distilling off the unreacted benzene, ethylbenzene and polyethylbenzene through reduced pressure distillation.

In this fraction, 85% by weight of 1-(3-ethylphenyl)-1-phenylethane was contained. Besides this compound, other components such as tetralin, indane, naphthalene, fluorene, alkyl derivatives of them and substances, the structures of which were unknown, were also contained in this fraction.

Dehydrogenation

A dehydrogenation catalyst (trademark: 64C made by Nissan Girdler Catalysts Co., Ltd.) of 0.5 to 1 mm in particle diameter was fed into a fixed bed continuous flow reactor made of a stainless steel tube of 10 mm in inner diameter and 60 cm in length, thereby forming a catalyst bed of 20 cm in height. An oily substance containing 82% of 1-(3-ethylphenyl)-1-phenylethane and pure water in a ratio of 1:5 were preheated respectively to be vaporized, and they were mixed together and fed to the catalyst bed at a temperature of 550° C. and an SV of 0.25. Reaction product was cooled to room temperature and the vapor phase and liquid phase were separated to obtain an organic layer, which was subjected to reduced-pressure distillation at 2 to 3 mmHg to obtain a fraction of 133° to 137° C. As a result of GC analysis, it was understood that the fraction contained 86% by weight of 1-(3-vinylphenyl)-1-phenylethylene (formula III) and 14% by weight of other hydrocarbons.

The analytical data in connection with the refined product of 1-(3-vinylphenyl)-1-phenylethylene (formula III) was coincident with the data in Example 1.

EXAMPLE 4

Synthesis of α-(3-(1-phenylethenyl)phenyl)propionic acid methyl ester

To a 500 ml autoclave with a stirrer was added 43 g of 1-(3-vinylphenyl)-1-phenylethylene, 0.74 g of palladium chloride (II), 2.19 g of triphenylphosphine, 13.4 g of methyl alcohol and 90 ml of toluene as a solvent. The pressure was raised up to 150 kg/cm$^2$ by carbon monoxide at room temperature. Further, the temperature was raised to 125° C. and the pressure was raised simultaneously to 400 kg/cm$^2$. After the absorption of carbon monoxide by the reaction ceased, the reaction was still continued for 16 hours. After the reaction, the reaction mixture was subjected to reduced-pressure distillation at 2 to 3 mmHg to obtain α-(3-(1-phenylethenyl)phenyl)propionic acid methyl ester having a boiling point of 144.5° to 145.5° C. at 2 to 3 mmHg was obtained in a yield of 87% (on the basis of 1-(3-vinylphenyl)-1-phenylethylene). The data of spectrum analysis are shown.

IR: (Neat) cm$^{-1}$ 3040, 2995, 2960, 2880, 2850, 1780; 1610, 1500, 1445, 1340, 1260, 1190; 1075, 1032, 905, 785, 710.

$^1$H-NMR: (CCl$_4$, δppm) 6.70–7.30 (9H Multiplet); 5.32 (2H Singlet); 3.20–3.75 (4H Multiplet); 1.45–1.56 (3H, Doublet).

Elemental Analysis: (as $C_{18}H_{18}O_2$)
Calculated: C: 81.20%; H: 6.77%; O: 12.03%.
Found: C: 81.20%; H: 6.80%; O: 12.00%.

EXAMPLE 5

Synthesis of α-(3-benzoylphenyl)propionic acid (ketoprofen)-(1)

α-(3-(1-Phenylethenyl)phenyl)propionic acid (35 g) obtained in Example 2 was dissolved in 250 ml of benzene and 250 ml of water was further added thereto with vigorous stirring to prepare a suspension. Then, 2 liter of 2% aqueous solution of potassium permanganate was dropped little by little over 1.5 hours. After the dropping, stirring was continued for 18 hours at room temperature. After the reaction, it was acidified by adding concentrated sulfuric acidand was treated by adding 35 g of sodium sulfite. After that, 500 ml of water was added and extraction was carried out three times with 150 ml of ether. The ether solution was washed with water and it was extracted three times with 200 ml of 5% aqueous solution of sodium hydroxide. The aqueous layer was then acidified by adding hydrochloric acid and extracted again three times with 150 ml of ether, which was followed by washing with water, drying with anhydrous magnesium sulfate, and filtration. The ether was then removed by reduced-pressure evaporation. Finally, 20 g of α-(3-benzoylphenyl)-propionic acid (ketoprofen) was obtained by re-crystallization from benzene/petroleum ether mixture. The melting point and spectrum were the same as those of an authentic sample.

EXAMPLE 6

Synthesis of α-(3-benzoylphenyl)propionic acid (ketoprofen)-(2)

α-(3-(1-Phenylethenyl)phenyl)propionic acid methyl ester (36 g) obtained in Example 4 was dissolved in 250 ml of benzene and 250 ml of water was further added thereto with vigorous stirring to prepare a suspension. Then, 2 liter of 2% aqueous solution of potassium permanganate was dropped little by little over 1.5 hours. After the dropping, stirring was continued for 18 hours at room temperature. After the reaction, it was acidified by adding concentrated sulfuric acid and was treated by adding 35 g of sodium sulfite. After that, 500 ml of water was added and extraction was carried out three times with 150 ml of ether. The ether solution was washed with water and it was added to 5% aqueous solution of sodium hydroxide. The aqueous solution was hydrolyzed at the refluxing temperature for 5 hours. After cooling, the solution was extracted with ether. The aqueous layer was acidified by adding hydrochloric acid and extracted again with ether, which was a followed by washing with water, drying with anhydrous magnesium sulfate, and filtration. The ether was then removed by reduced-pressure evaporation. Finally, 20 g of α-(3-benzoylphenyl)propionic acid (ketoprofen) was obtained by re-crystallization from benzene/petroleum either mixture. The melting point and spectrum were the same as those of an authentic sample.

EXAMPLE 7

Synthesis of α-(3-(1-phenylethenyl)phenyl)propionic acid tert-butyl ester

Hydroesterification of 1-(3-vinylphenyl)-1-phenylethylene with tert-butyl alcohol was carried out in the like manner as in Example 4. The yield of the obtained α-(3-(1-phenylethenyl)phenyl)propionic acid tert-butyl ester was 50% on the basis of the starting olefin. The analytical data on the obtained α-(3-(1-phenylethenyl)phenyl)propionic acid tert-butyl ester are shown in the following.

Boiling Point: 172°–174° C./2–3 mmHg
IR: (Neat) cm$^{-1}$ 3045, 2990, 2955, 1745, 1490, 1370; 1260, 1150, 915, 875, 820, 775; 715.

$^1$H-NMR: (CCl$_4$, δppm) 6.75–7.30 (9H Multiplet) 5.32 (2H Singlet) 3.50 (1H Quadruplet) 1.58 (9H Singlet) 1.41–1.53 (3H Doublet)

Elemental Analysis: (as $C_{21}H_{24}O_2$)
Calculated: C: 81.82%; H: 7.79%; O: 10.39%. Found: C: 81.80%; H: 7.80%; O: 10.40%.

Then, 36 g of the obtained α-(3-(1-phenylethenyl)-phenyl)propionic acid tert-butyl ester was oxidized in the like manner as in Example 6, which was followed by hydrolysis and re-crystallization to obtain 23 g of α-(3-benzoylphenyl)propionic acid (ketoprofen). The melting point and the spectrum of this product were the same as those of an authentic sample.

EXAMPLE 8

Synthesis of α-(3-benzoylphenyl)propionic acid (ketoprofen)

To a 300 ml reaction vessel with a stirrer were fed 15 g of α-(3-(1-phenylethenyl)phenyl)propionic acid obtained in Example 2, 0.03 g of cobalt naphthenate and 100 ml of acetic acid as a solvent and 150 ml/min of pure oxygen was fed into the vessel for 16 hours at a reaction temperature of 120°. After the reaction, the solvent was removed by reduced-pressure distillation to obtain a solid substance. The solid substance was washed five times with 500 ml of water and it was dissolved in 500 ml of ether and washed three times again with water. After that, the ether was removed by reduced-pressure distillation and the product was finally recrystallized with benzene/petroleum ether mixture to obtain 9.8 g of α-(3-benzoylphenyl)propionic acid (ketoprofen). The properties such as melting point and the spectrum of the final product were the same as those of an authentic sample.

What is claimed is:

1. α-(3-(1-Phenylethenyl)phenyl)propionic acid or its alkyl ester which is represented by the following formula (II):

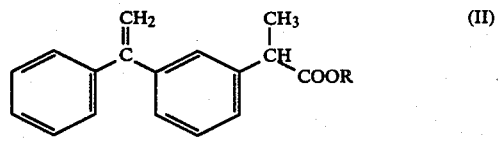

wherein R is a hydrogen atom or a lower alkyl group having 1 to 4 carbon atoms.

2. The alkyl ester in claim 1, wherein said lower alkyl group is a methyl group.

* * * * *

UNITED STATES PATENT AND TRADEMARK OFFICE
CERTIFICATE OF CORRECTION

PATENT NO. : 4,937,375

DATED : June 26, 1990

INVENTOR(S) : Osoo Shimizu, et al.

It is certified that error appears in the above-identified patent and that said Letters Patent is hereby corrected as shown below:

Column 3, line 2: "obtaine" should read as --obtained--

Column 3, line 37: "aspect" should read as --object--

Column 5, line 15: "novel" should read as --noble--

Column 10, line 51: "to" should read as --by--

Column 11, lines 2-3" "yield 89%" should read as --yield of 89%--

Column 13, line 1: "1780;" should read as --1740;--

Signed and Sealed this

Twelfth Day of November, 1991

Attest:

HARRY F. MANBECK, JR.

Attesting Officer

Commissioner of Patents and Trademarks